United States Patent [19]

Cottman

[11] 4,020,042
[45] Apr. 26, 1977

[54] PHENOLIC ANTIOXIDANTS
[75] Inventor: Kirkwood S. Cottman, Akron, Ohio
[73] Assignee: The Goodyear Tire & Rubber Company, Akron, Ohio
[22] Filed: Nov. 20, 1974
[21] Appl. No.: 525,439
[52] U.S. Cl. .................. 260/45.85 H; 260/481 R
[51] Int. Cl.² .................. C08K 5/37; C07C 5/00
[58] Field of Search .............. 260/45.85 H, 481 R, 260/45.85 S, 45.95 F

[56] References Cited
UNITED STATES PATENTS

| | | | |
|---|---|---|---|
| 2,951,052 | 8/1960 | Darby | 260/45.95 F |
| 3,144,422 | 8/1964 | Homberg | 260/45.85 H |
| 3,496,211 | 2/1970 | Dexter et al. | 260/45.9 R |
| 3,536,661 | 10/1970 | Hagemeyer et al. | 260/481 R |
| 3,637,809 | 1/1972 | Kleiner | 260/45.85 H |
| 3,644,485 | 2/1972 | Lappin et al. | 260/481 R |
| 3,676,471 | 7/1972 | Eggensperger et al. | 260/481 R |
| 3,795,700 | 3/1974 | Song et al. | 260/481 R |
| 3,829,481 | 8/1974 | Kauffman | 260/481 R |

*Primary Examiner*—V. P. Hoke
*Attorney, Agent, or Firm*—F. W. Brunner; J. A. Rozmajzl

[57] ABSTRACT

A phenolic antioxidant is combined with a sulfur-containing compound to form a larger antioxidant molecule. The resulting compounds are non-staining and prevent polymer degradation.

4 Claims, No Drawings

PHENOLIC ANTIOXIDANTS

This invention relates to a composition of matter having an improved stabilizing effect on oxidizable organic materials. More particularly this invention relates to new phenolic antioxidants and to polymer compositions containing these materials and to a method of preparing these materials by reacting a phenolic compound with compounds capable of producing a phenolic ester thiol.

The prior art teaches that oxidative protection has been obtained by mechanically mixing antioxidants functioning by different mechanisms into the oxidizable organic polymers. Such antioxidant compounds are frequently lost to the organic material by extraction and evaporation thus altering the optimum concentration of each needed for the best antioxidant effect.

It is an object of the present invention to provide a process of manufacturing an antioxidant. It is a further object of this invention to provide an antioxidant that prevents oxidative degradation of polymers. Further objects will become evident to those skilled in this art as the description proceeds.

The phenolic starting materials of this invention have a structural formula selected from the group consisting of

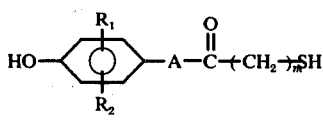

and

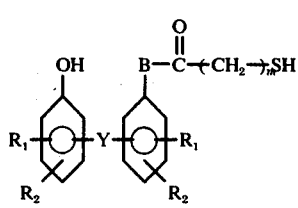

wherein $R_1$ and $R_2$ are the same or different radicals selected from the group consisting of hydrogen, alkyl radicals containing from 1 to 10 carbon atoms, cycloalkyl radicals containing from 5 to 8 carbon atoms, aralkyl radicals containing from 7 to 9 carbon atoms and substituted and unsubstituted aryl radicals containing from 6 to 8 carbon atoms, m is 1 or 2, A is selected from the group consisting of —K—X—, —X—Z—X— or T—Z—X— wherein K is an alkylene radical containing from 1 to 10 carbon atoms, Z is an alkylene radical containing from 2 to 10 carbon atoms, X is oxygen, T is sulfur and B is —X—Z—X—, Y is a bivalent radical selected from the group consisting of C=O, —O—, —S— and alkylene radicals containing 1 to 5 carbon atoms.

The compounds described above can be prepared by reacting phenolic compounds containing reactive hydroxyl groups having a general structural formula selected from the group consisting of

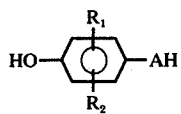

and

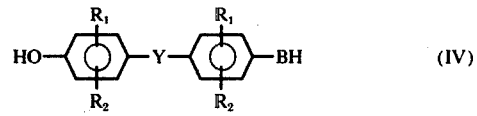

with ester forming compounds having the general formula $$EO-\overset{O}{\underset{\|}{C}}-(CH_2)_m-SH \qquad (V)$$

wherein $R_1$, $R_2$, B, Y, m and A are the same as described above and E is selected from the group consisting of hydrogen and alkyl radicals containing from 1 to 3 carbon atoms.

The reaction can be catalyzed by small amounts of acidic catalyst, although catalysts may not be necessary in some reactions. The amount of catalyst used can vary widely. However from 0.25 gram to 5.0 grams of catalyst per 100 grams of reactants is usually sufficient. Higher levels of catalyst can be used but usually yield no advantage. Representative examples of acidic catalysts useful in the present invention are toluenesulfonic acid, sulfuric acid, boron trifluoride, benzenesulfonic acid, hydrochloric acid, phosphoric acid, ion exchange resins and acid-activated clays.

The reaction may be run without solvent. However solvents such as xylene, benzene or toluene usually aid in carrying out the reaction. The reaction can be run at room temperature, but usually is run at a temperature up to the boiling point of the solvent. If no solvent is used the reaction is carried out below the boiling point of the reactants.

The molar ratio of phenolic to ester forming compound is 1:1, however excess ester forming compound may be used to speed up the reaction and reduce side reactions. Any amount of excess ester forming compound can be used; however molar ratios of phenolic to ester forming compound of from 1:1 to 1:2 are preferred.

Representative examples of phenolic starting materials useful in this invention are:
3-(3,5-ditert.butyl-4-hydroxyphenyl)-1-propanol
3,5-ditert.butyl-4-hydroxybenzyl alcohol
3-(3,5-ditert.butyl-4-hydroxyphenyl)-2-butanol
10-(3,5-ditert.butyl-4-hydroxyphenyl)-1-decanol
3,5-ditert.butyl-4-hydroxyphenoxyethanol
3,5-ditert.butyl-4-hydroxyphenylthio ethanol
3[2-(3,5-ditert.hexyl-4-hydroxybenzyl)-4-ethyl phenoxy] 1-propanol
3-(3,5-ditert.butyl-4-hydroxyphenyl)-2,2-dimethyl-1-propanol
3-(3-decyl-4-hydroxyphenyl)-2-butanol
2-(3,5-dicyclopentyl-4-hydroxyphenyl)-1-ethanol
2-cyclooctyl-4-hydroxybenzyl alcohol
4-(3,5-di-α-phenylethyl-4-hydroxyphenyl)-1-butanol
2-(3,5-α,α-dimethylbenzyl-4-hydroxyphenyl)-1-pentanol
2-(2-hydroxy-3-tert.butyl-5-methylphenylthio)-4-methyl-6-tert.butyl phenoxyethanol
3,5-dimethyl-4-hydroxybenzyl alcohol
2,(2-hydroxy-3-tert.butyl-5-methylphenyl carbonyl)-4-methyl-6-tert.butyl phenoxyethanol Representative examples of compounds produced using the process of the present invention are:

[3-(3,5-ditert.butyl-4-hydroxyphenyl)propyl] 3-mercaptopropionate

[2-(3,5-ditert.butyl-4-hydroxybenzyl)-4-methylphenoxyethyl] 3-mercaptopropionate 3,5-ditert.-4-hydroxybenzyl mercaptoacetate

[2-(2-hydroxy-3-tert.butyl-5-methylphenylthio)-4-methyl-6-tert.butylphenoxyethyl] 3-mercaptopropionate

[2-(2-hydroxy-3-decyl-5-methylbenzyl)-4-methyl-6-tert.butylphenoxypropyl] 3-mercaptopropionate 3,5-ditert.butyl-4-hydroxybenzyl 3-mercaptopropionate 3-methyl-4-hydroxy-5-cyclooctylbenzyl 3-mercaptopropionate

[10-(3,5-ditert.hexyl-4-hydroxyphenyl)decyl] 3-mercaptopropionate

[3-(3,5-ditert.butyl-4-hydroxyphenyl)-2,2-dimethylpropyl] 3-mercaptopropionate

[2-(2-hydroxy-3-tert.butyl-5-methyl-α,α-diethylbenzyl)-4-methyl-6-tert.butyl phenoxyethyl] 3-mercaptopropionate

[3-cyclopentyl-4-hydroxybenzyl] mercaptoacetate

[3,5-ditert.butyl-4-hydroxyphenylthioethyl] 3-mercaptopropionate

[2-(2-hydroxy-3-tert.butyl-5-methylphenylcarbonyl)-4-methyl-6-tert.butyl phenoxyethyl] 2-mercaptopropionate

[2-(3,5-ditert.butyl-4-hydroxybenzyl)-4-ethylphenylphenoxypropyl] mercaptoacetate Representative examples of ester forming compounds are:

3-mercaptopropionic acid
2-mercaptopropionic acid
mercaptoacetic acid
propyl, 3-mercaptopropionate
methyl, 2-mercaptopropionate ethyl, mercaptoacetate The compounds of this invention are useful in clear polymers such as polypropylene and polyethylene because of their clarity. These compounds also are superior to those known in the prior art for preventing the hardening of oxidizable polymers. These compounds in addition may function as chain transfer agents. The free thiol (-SH) group allows these compounds to be chemically incorporated to some extent, into polymers during processing. The compound can prevent hardening in styrene-butadiene polymers.

Generally the stabilizers of this invention are employed from about 0.0005 percent to about 10 percent by weight of the stabilized composition, although this will vary with the particular polymer. A particularly advantageous range is from about 0.025 percent range to about 1.5 percent. The compounds are especially useful for the stabilization of polyethylene and polypropylene but are also effective in olefin polymers.

The example given below illustrate typical procedures used to produce a phenolic antioxidant.

EXAMPLE 1

Fifty-three grams of 3-(3,5-ditert.butyl-4-hydroxyphenyl)-1 propanol, 25.4 grams of 3-mercaptopropionic acid, and one gram of toluene sulfonic acid were dissolved in 100 milliliters of benzene and heated to reflux. After 2½ hours at reflux, 4 milliliters of water had been collected. Thin layer chromatography indicated that all the phenolic alcohol had reacted. The reaction product was washed with water, decanted and stripped to a reactor temperature of 80° C. at 15 millimeters of mercury. The sulfur content of the [3-(3,5-ditert.butyl-4-hydroxyphenyl) propyl] 3-mercaptopropionate was 9.3 percent as opposed to a theoretical sulfur content of 9.1 percent.

EXAMPLE 2

Two hundred and twenty-one grams of mercaptoacidic acid, 2 grams of toluene sulfonic acid and 94.4 grams of 3,5-ditert.butyl-4-hydroxybenzyl alcohol were placed in a flask equipped with thermometer, water condenser and agitator. The reaction product was stirred for one hour at room temperature and then allowed to stand for 16 hours without further agitation. The reaction product was washed with warm water. The benzene solvent was stripped off until the reaction product crystallized in the form of white crystals. Hexane was then added to wash the white crystals. The 3,5-ditert.butyl-4-hydroxybenzyl mercaptoacetate had a melting point of from 107.5° to 108.5° C.

EXAMPLE 3

27.9 Grams of 3-(3,5-ditert.butyl-4-hydroxyphenyl)-2-butanol, one gram of toluene sulfonic acid and 21.2 grams of 3-mercaptopropionic acid were dissolved in 120 milliliters of benzene. The reaction mixture was heated to reflux and the water formed was collected. After 5 hours of reflux at 84° C. a total of 2 milliliters of water had been collected. Thin layer chromatography indicated that all the phenolic alcohol had reacted. The reaction product was washed with warm water and then the volatiles were stripped off at 75° C. under vacuum.

EXAMPLE 4

Fifty grams of 2,2-dimethyl-3-(3,5-ditert.butyl-4-hydroxyphenyl)-1-propanol, 1.0 gram of toluenesulfonic acid, 100 milliliters of benzene and 27 grams of 3-mercaptopropionic acid were heated to reflux using a water trap. After refluxing two hours, the reaction was complete. The reaction product was washed with 50 milliliters of water and decanted. The benzene solution was cooled to 8° C., then filtered and washed with hexane. The white [2,2'-dimethyl-3-(3,5-ditert.butyl-4-hydroxyphenyl) propyl] 3-mercaptopropionate had a melt temperature of 105° to 106° C.

Table I

| Antioxidant one part used | Oxygen Absorption at 100° C. Hours to Absorb 1% O₂ In SBR-1006 |
|---|---|
| No antioxidant (control) | 10 |
| Example 1 | 445 |
| Example 2 | 427 |
| Example 3 | 419 |
| (3,5-ditert.butyl-4-hydroxybenzyl) 3-mercaptopropionate | 456 |

A compound of this invention was also tested for color characteristics in polypropylene and compared to a clear polypropylene containing no antioxidant. Profax 6501 is clear polypropylene containing no stabilizer and sold by Hercules Chemical Company.

The symbols used measure various coloring characteristics as defined below.

The symbol Rd is a measure of reflectance on the Gardner Colorimeter based upon a MgO standard given the value of 91.1. This value indicates position along a neutral color axis from black to white with high values indicating high reflectance or brightness.

The symbol "a" is an expression of the dominant colors of red (if a positive value) and of green (if a negative value). Intensity of either color is indicated by the magnitude of the value regardless of sign. The standard is magnesium oxide given the value of 0.0.

The symbol "b" is an expression of the dominant colors of yellow (if a positive value) and of blue (if a negative value). Intensity of either color is indicated by the magnitude of the value regardless of sign. The standard is magnesium oxide given the value of 0.0.

The color index is a measure of the total polymer color characteristics and is calculated by $$\frac{Rd}{(a+b)}.$$

Table II

| Color Characteristics | | |
|---|---|---|
| Profax 6501 | 100.00 | |
| Example 1 | | 0.30 |
| Original | | |
| Rd | 56.6 | 55.7 |
| a | −1.0 | −1.1 |
| b | +5.8 | +6.7 |
| Color Index | 8.3 | 7.2 |
| Oven Aged 1 Day at 140° C. | | |
| Rd | 53.9 | 51.1 |
| a | −1.2 | −1.7 |
| b | +6.7 | +9.1 |
| Color Index | 6.8 | 4.7 |
| Oven Aged 3 Days at 140° C. | | |
| Rd | CRAZED | 47.9 |
| a | FAILED | −1.8 |
| b | | +18.5 |
| Color Index | | 2.4 |
| Oven Aged 10 Days at 140° C. | | |
| Rd | CRAZED | 43.0 |
| a | FAILED | 0.0 |
| b | | +21.0 |
| Color Index | | 2.0 |
| Days to Failure at 140° C. | | |
| Craze | 2 | 41 |
| Destruction | 6 | 49 |

While certain embodiments and details have been shown for the purpose of illustrating the invention, it will be apparent to those skilled in this art that various changes and modifications may be made herein without departing from the spirit or the scope of this invention.

I claim:

1. Phenolic compounds with a structural formula selected from the group consisting of

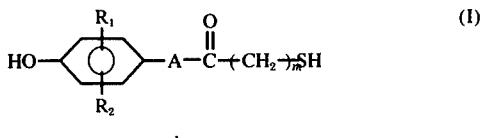

and

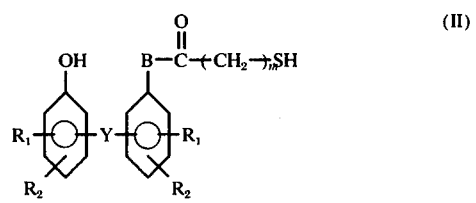

wherein $R_1$ and $R_2$ are the same or different radicals selected from the group consisting of hydrogen, alkyl radicals having from 1 to 10 carbon atoms, cycloalkyl radicals having from 5 to 8 carbon atoms, aralkyl radicals having from 7 to 9 carbon atoms, and substituted and unsubstituted aryl radicals containing from 6 to 8 carbon atoms, $m$ is 1 or 2, A is selected from the group consisting of —K—X—, —X—Z—X— or —T—Z—X— and B is —X—Z—X— wherein K is an alkylene group containing from 1 to 10 carbon atoms, Z is an alkylene radical containing from 2 to 10 carbon atoms, X is oxygen, T is sulfur, Y is a bivalent radical selected from the group consisting of —O—, —S— and alkylene radicals containing from 1 to 5 carbon atoms.

2. Polypropylene according to claim 1 wherein the compound is selected from the group consisting of (3,5-di-t-butyl-4-hydroxybenzyl) 2-mercaptopropionate, 4-(3,5-di-t-butyl-4-hydroxyphenyl)-2-butyl 3-mercaptopropionate, 3-(3,5-di-t-butyl-4-hydroxyphenyl) propyl 3-mercaptopropionate, (3,5-di-t-butyl-4-hydroxybenzyl) 2-mercaptoacetate and 3-(3,5-di-t-butyl-4-hydroxyphenyl)-2,2-dimethylpropyl 3-mercaptopropionate.

3. An olefin polymer having incorporated therein in an antioxidant amount a compound according to claim 1.

4. Polypropylene having incorporated therein in an antioxidant amount a compound according to claim 1.

* * * * *